United States Patent [19]
Krepinsky et al.

[11] Patent Number: 5,616,698
[45] Date of Patent: Apr. 1, 1997

[54] POLYMER-SUPPORTED SOLUTION SYNTHESIS OF OLIGOSACCHARIDES

[75] Inventors: Jiri J. Krepinsky, Newmarket; Stephen P. Douglas, Scarborough; Dennis M. Whitfield, Toronto, all of Canada

[73] Assignee: University of Toronto Innovations Foundation, Toronto, Canada

[21] Appl. No.: 179,096

[22] Filed: Jan. 10, 1994

[51] Int. Cl.⁶ .............. C07G 3/00; C07H 1/00; C07H 15/04; C08B 37/00
[52] U.S. Cl. ............ 536/18.6; 536/123.1; 536/123.13; 536/124; 536/120
[58] Field of Search ............... 536/18.6, 123.1, 536/123.13, 124, 120

[56] References Cited

U.S. PATENT DOCUMENTS

| | | | |
|---|---|---|---|
| 3,173,892 | 3/1965 | Kun | 525/153 |
| 3,853,708 | 12/1974 | Porath et al. | 435/179 |
| 3,941,849 | 3/1976 | Herold | 568/620 |
| 4,029,720 | 6/1977 | Seiler et al. | 525/89 |
| 4,083,834 | 4/1978 | Komatsu et al. | 525/346 |
| 4,085,168 | 4/1978 | Milkovich et al. | 525/59 |
| 4,609,546 | 9/1986 | Hiratani | 424/78.3 |
| 4,908,405 | 3/1990 | Bayer et al. | 525/61 |
| 5,180,674 | 1/1993 | Roth | 435/288 |

FOREIGN PATENT DOCUMENTS

| | | |
|---|---|---|
| 1290481 | 10/1991 | Canada. |
| 2077297 | 1/1971 | France. |
| 2195641 | 8/1973 | France. |
| 2435642 | 7/1971 | Germany. |
| 879950 | 10/1961 | United Kingdom. |
| 1002343 | 8/1965 | United Kingdom. |

OTHER PUBLICATIONS

Bayer, E. Towards the Chemical Synthesis of Proteins *Angew. Chem. Int. Ed.* 1991 30:113–216.

Bayer et al. Liquid Phase Synthesis of Peptides *Nature* 1972 237:512.

Bonora et al. Large scale, liquid phase synthesis of oligonucleotides by the phosphoramidite approach *Nucleic Acids Res* 1993 21:1213–1217.

Bonora et al. HELP (High Efficiency Liquid Phase) new oligonucleotide synthesis on soluble polymeric support *Nucleic Acids Res* 1990 18:3155.

Danishefsky et al. A Strategy for the Solid–Phase Synthesis of Oligosacchardies *Science* 1993 260:1307.

Douglas et al. Polymer–Supported Solution Synthesis of Oligosaccharides *Am. Chem. Soc.* 1991 113:5095.

Frechet J. Synthesis and Application of Organic Polymers as Supports and Portecting Groups *Tetrahedron* 1981 37:663.

Frechet J. Polymer–supported Synthesis of Oligosaccharides *Polymer–Supported Reactions in Organic Synthesis* 1980 Ch 8, 407.

Frechet J. Synthesis Using Polymer–supported Protecting Groups *Polymer–Supported Reactions in Organic Synthesis* 1980 Ch 6, 293.

Frechet et al. Solid–Phase Synthesis of Oligosaccharides *Carbohydr. Res.* 1991 22:399.

(List continued on next page.)

*Primary Examiner*—Gary E. Hollinden
*Assistant Examiner*—Everett White
*Attorney, Agent, or Firm*—Woodcock Washburn Kurtz Mackiewicz & Norris

[57] ABSTRACT

The present invention provides improved syntheses of oligosacchairdes. In accordance with preferred embodiments, anomeric specificity in such syntheses can be attained using polymer-supported liquid synthetic design with certain novel diether linkers. The present invention also provides novel strategies for capping imcompletely glycosylated hydroxyls.

35 Claims, 1 Drawing Sheet

OTHER PUBLICATIONS

Frechet et al. Solid–Phase Synthesis of Oligosaccharides *J. Am. Chem. Soc.* 1971, 93;492.

Friesen et al. On the Use of the Haloetherification Method to Synthesize Fully Functionalized Disaccharides *Tetrahedron* 1990 46:103–112.

Friesen et al. On the Controlled Oxidative Coupling of Glycals *J. Am. Chem. Soc.* 1989 111:6656–6660.

Fugedi et al. Thioglycosides as Glycosylating Agents in Oligosaccharide Synthesis *Glycoconjugate J.* 1987 4:97.

Ichikawa et al. Chemical–Enzymatic Synthesis and Conformational Analysis of Sialyl Lewis x and Derivatives *J. Am. Chem. Soc.* 1992 114:9283–9298.

Kamaike et al. Efficient Syntheses of An Oligonucleotide on A Cellulose Acetate Derivative As A Novel Polymer–Support Using Phosphotriester Approach *Tetrahedron* 1988 29:647–650.

Kanie et al. Glycosylation Using Methythioglycosides fo N–Acetylneuraminic Acid and Dimethyl Sulfonium triflate *J. Carbohy. Chem.* 1988 7:501.

Kaur et al. Use of N–Acetylglucosaminyltransferases I and II in the preparative synthesis of oligosaccharides *Carbohy. Res.* 1991 210:145–153.

Look et al. A Combined Chemical and Enzymatic Strategy for the Construction of Carbohydrate–Containing Antigen Core Units *J. Org. Chem.* 1993 58:4326.

Mathur et al. Oligosaccharide Synthesis on Polymer Supports Polymers as Aids in Organic Chemistry Academic Press New York, 1980 Ch 6, 105.

Mereyala et al. Stereoselective Synthesis of α–Linked Saccharides *Tetrahedron* 1991 47:6435–6448.

Mootoo et al. n–Pentenyl Glyosides Permit the Chemospecific Liberation of the Anomeric Center Am. Chem. Soc. 1988 110:2662–2663.

Mutter et al. The Liquid–Phase method for Peptide Synthesis *The Peptides* Academic Press: New York 1980 Ch. 2, 286.

Paulsen H. Syntheses, Conformations and X–Ray Structure Analyses of the Saccharide Chaims from the Core Regions of Glycoproteins *Angew. Chem. Int. Ed.* 1990 29:823.

Paulsen H. Advances in Selective Chemical Syntheses of Complex Oligosaccharides *Angew. Chem. Int. Ed.* 1982 21:155.

Schmidt R. New Methods for the Synthesis of Glycosides and Oligosaccharides *Angew. Chem. Int. Ed.* 1986 25:212.

Toshima et al. Recent Progress in O–Glycosylation Methods and Its Application to Natural Products Synthesis *Chem Rev.* 1983 93:1503–1531.

Wong et al. Enzymatic Synthesis of N–and O–Linked Glycopeptides *J. Am. Chem. Soc.* 1993 115:5893.

Wong et al. Probing the Acceptor Specificity of β–1,4–Galactosyltransferase for the Development of Enzymatic Synthesis of Novel Oligosaccharides, *J. Am. Chem. Soc.,* 1991, 113, pp. 8137–8145.

Veenerman et al. Synthesis of Carbohydrate–Antigenic Structures of Mycobacterium Tuberculosis Using and Iodonium Ion Promoted Gylcosidation Approach *J. Carbohy. Chem.* 1990 9:783–796.

Zehavi U. Applications of Photosensitive Protecting Groups in Carbohydrate Chemistry *Advances in Carbohy. Chem. Biochem.* 1988 46:179.

5,616,698

POLYMER-SUPPORTED SOLUTION SYNTHESIS OF OLIGOSACCHARIDES

FIELD OF THE INVENTION

This invention relates to the preparation of oligosaccharides, using a polymer supported methodology. By this method, in which the growing oligosaccharide chain is linked to a supporting high-molecular weight substrate, and which offers easy purification and sufficient anomeric control, oligosaccharides are produced in comparable yields with known methodologies but very rapidly. The linker between the polymers and the synthesized oligosaccharide is a particularly important part of the synthetic system since it has to be very stable during all chemical operations required for the synthesis and must be removable with ease at the end of the synthesis.

BACKGROUND OF THE INVENTION

Oligosaccharides occurring naturally in glycolipids, glycoproteins, or proteoglycans have many important biological functions. The carbohydrate portion (usually one or more oligosaccharides) of the molecule may have many roles, e.g. it serves as a recognition signal (it directs the glycoconjugate to a particular site, both in cells and multicellular organisms, at which the function of the glycoconjugate is executed), mediates adhesion of pathogenic bacteria to tissues (a necessary condition for an infectious process to take place), and mediates metastasis in neoplasia. New types of therapeutics and vaccines for inflammatory diseases (arthritis), bacterial infections, and cancer, based on oligosaccharides, are being developed. The utilization of oligosaccharides as disease-preventive agents is under active consideration. The need for various oligosaccharides has never been greater in biomedical sciences and industries. Unfortunately, it is not practical to obtain oligosaccharides from natural sources since they occur in very small quantities in complicated mixtures difficult to separate into individual components. Thus the efficient preparation of oligosaccharides, and their elaboration into glycopeptides and glycolipids, must be carried out by synthesis, organic chemical synthesis being the ultimate strategy. Oligosaccharides may be further elaborated into glycopeptides and glycolipids which have important utility on their own in the fields of medicine, biotechnology, food, and related technologies.

DESCRIPTION OF RELATED ART

Oligosaccharides have been synthesized by solution methodologies for many years, and more recently by methods employing enzymes. The solution methodologies of oligosaccharide synthesis made dramatic advancements during the past few years but yields in the key glycosidic linkage formation steps are still in the 80% range at best. In addition, each glycosidic linkage can form two stereoisomers (anomers) and this anomericity must be controlled. However, control of anomeric specificity of glycosylation reactions was established in certain situations through the use of participating groups. Also, certain "difficult linkages" are accessible in much lower yield, often below 50%. This reflects both the low reactivity and the instability of the reactants, in particular of the glycosylating agent. The activated glycosylating agent may decompose to several products, behaving chromatographically similar to the desired product. The excess glycosylating agent necessary to obtain an acceptable yield of coupled products often leads to reaction mixtures in which the desired compound is a relatively minor component. Thus a major obstruction to greater efficiency of glycosylation is the chromatographic purification.

Methods employing enzymes for synthesis of oligosaccharides have been disclosed as well. The enzymes are either glycosyl transferases or glycosidases that normally function in the biosynthesis of oligosaccharides in living cells. Glycosyl transferases and glycosidases are increasingly more available by cloning and their utility depends on their specificity and on the availability of glycosyl donors (e.g., monosaccharide nucleotides; not at all easy to make even using their regeneration). The art of using enzymes for the in vitro synthesis of oligosaccharides has been described in many publications and patents. A major obstacle in using the enzyme methodology is the difficulty in obtaining glycosyl nucleotides in sufficient quantity and in purification of the final product.

Combined enzyme and solution chemistry strategies have also been described for preparations of specific oligosaccharides.

Solid-state synthesis of oligosaccharides using immobilized acceptor molecules has been described in publications and reviews. Among the problems encountered in using this methodology were: decreased glycosylation reaction rates compared to solution strategies, incomplete coupling, and lack of complete stereoselectivity. Since two epimers (anomers) can be formed, stereochemical control is mandatory for successful synthesis. Solid state synthesis using glycal chemistry has been disclosed recently. The last mentioned methodology can be described as reversed glycosylation since the glycosylating agent is immobilized and a soluble acceptor molecule is used in contrast with previous strategies using immobilized acceptor molecule and a soluble glycosylating agent.

Polymer-supported liquid synthesis of peptides and oligonucleotides using polyethyleneglycol monomethylether (PEG) as support for the synthesis of oligomers of peptides and nucleotides has been described. Although in this reaction design the reactants are soluble in the reaction medium during the reaction itself, this methodology had not been considered for oligosaccharide syntheses.

In our U.S. Pat. No. 5,278,303, we have shown that in the polyethylene glycol (polyethyleneglycol monomethylether [$HOCH_2CH_2(OCH_2CH_2)_nOCH_3$], where n is 80–160; PEG, average MW 5,000) supported synthesis of oligosaccharides, good anomeric specificity can be achieved by judicious application of chemical principles of oligosaccharide synthesis, without affecting other desirable facets of this synthetic design, i.e. the ease and speed with which the process is completed. In this approach a polymer-carbohydrate synthon is synthesized which is soluble under conditions of glycosylation, and insoluble during the work-up of the reaction mixtures. This guaranteed solubility of the polymer-containing reactants during the reactions allows for reaction kinetics and anomericity control similar to that observed in solution chemistry. The oligosaccharide comprises at least two monosaccharide units by definition. At least one of the monosaccharides is suitably derivatized so as to allow attachment to the PEG or a derivative thereof. The oligosaccharide must be capable of being elaborated into a substance which is suitable for subsequent glycosylation. The glycosylation is performed under standard liquid-phase chemistry conditions which are well known in the art and are, of course, contingent upon the monosaccharide units and their associated linkages. Monitoring of the glycosylation reaction is easily achieved through nuclear magnetic resonance spectrometry. The number of additions of glycosylating agent needed for reaction completion may be more than one. The glycosylation agent may be any saccharide as long as it has an activated anomeric centre.

In the U.S. patent mentioned above, we have shown that the polymer is connected with the growing oligosaccharide chain through linkages of a succinoyl diester tether to a carbohydrate hydroxyl. While this linker is satisfactory in many synthetic situations, there are some circumstances in which a more base-stable tether is needed. Furthermore, the succinoyl linker can migrate from one hydroxyl group to another, or cleave off, particularly from the anomeric centre, under certain acidic conditions.

SUMMARY OF THE INVENTION

We have now discovered that synthesis of oligosaccharides can be performed efficiently and with satisfactory anomeric specificity using a polymer-supported liquid synthesis design that utilizes a novel armoatic diether linker, —O—$CH_2C_6H_4CH_2$—O—. The synthesis also includes a novel strategy for capping incompletely glycosylated hydroxyls utilizing for example allyl trichloroacetimidate as the reagent. Finally the synthesis allows for the complete removal of the linker together with the supporting PEG, or partial removal by transformation of the linker into a benzyl-type of protecting group with concomitant loss of PEG. Consequently, we have discovered that synthesis of oligosaccharides can be performed efficiently and with satisfactory anomeric specificity using polymer-supported liquid synthesis design even under conditions which would formerly have lead to decomposition or loss of the desired products or reactants. Thus, albeit the synthetic design disclosed previously in the above noted patent is still perfectly valid, these new discoveries make it substantially more efficient to practice.

Thus the present invention provides a method for the preparation of oligosaccharides which comprises:

a) reacting as a first reactant, a saccharide having at least one monosaccharide unit and having a carbohydrate hydroxyl group and as a second reactant a monomethylether of polyethylene glycol linked to a tether having one free hydroxy group of a benzylic or allylic diol, and the linkage between the two reactants is an O-glycosidic linkage or an ether linkage;

b) activating the saccharide-polyethylene glycol derivative reaction product for glycosylation;

c) subjecting the activated saccharide-polyethylene glycol derivative reaction product to a glycosylation reaction through at least one addition of a glycosylating agent, while monitoring the reaction for completion;

d) capping any non-glycosylated hydroxyl with a capping agent which is more reactive than the glycosylating agent;

e) repeating, if necessary, steps b) to d);

f) isolating the polyethylene glycol-linker-oligosaccharide as a solid;

g) purifying the solid; and h) releasing the oligosaccharide from the polyethylene glycol-linker so that the carbohydrate hydroxyl becomes free; and when desired i) releasing the oligosacharide from the polyethylene glycol so that the linker becomes a p-methylbenzyl protecting group.

The saccharide hydroxyl may be an anomeric or non-anomeric hydroxyl.

In another aspect the invention provides a novel connection between the monomethylether of polyethylene glycol (PEG) and the saccharide made via a carbohydrate hydroxyl group (on the saccharide) through one oxygen of a diether group —O—$CH_2C_6H_4CH_2$—O— (DiOxyXylene, DOX). The linkage may be formed for example by reacting first α,α'-dichloroxylene with the PEG and the hydrolysis of the second chloride using an aqueous base, wherein PEG—O—$CH_2C_6H_4CH_2$—OH or its precursor PEGO—$CH_2C_6H_4CH_2$—Cl may be connected with the saccharide through the anomeric hydroxyl or another hydroxyl by methods well known in the art. Examples of such methods are shown in the subsequent Examples.

In yet another aspect the invention provides as a novel product the compound oligosaccharide linked to the polymer via the linker. These may be characterized as the reaction products obtained from the following steps:

a) reacting as a first reactant, a saccharide having at least one monosaccharide unit and having a carbohydrate hydroxyl group and as a second reactant a monomethylether of polyethylene glycol linked to a tether having one free hydroxy group of a benzylic or allylic diol, and the linkage between the two reactants is an O-glycosidic linkage or an ether linkage;

b) activating the saccharide-polyethylene glycol derivative reaction product for glycosylation;

c) subjecting the activated saccharide-polyethylene glycol derivative reaction product to a glycosylation reaction through at least one addition of a glycosylating agent, while monitoring the reaction for completion;

d) capping any non-glycosylated hydroxyl with a capping agent which is more reactive than the glycosylating agent;

e) repeating, if necessary, steps b) to d); and f) isolating the polyethylene glycol-linker-oligosaccharide as a solid;

These PEG glycosides of oligosaccharides are potentially important products because PEG may serve as the oligosaccharide carrier in many applications. Such applications comprise antigens for vaccinations, glycotherapeutics for diseases untreatable with conventional means such as cancer, arthritis, and cystic fibrosis, or diseases requiring treatment with less toxic agents such as early childhood Otitis media, drug carriers for site specific delivery, and food additives boosting prevention of bacterial infections, but applications are not limited to these examples.

The saccharide comprises both an oligosaccharide formed from at least two monosaccharide units by definition, or a monosaccharide. One of the monosaccharide units, or a monosaccharide, must be suitably derivatized so as to allow attachment to the PEG or a derivative thereof. The saccharide must be capable of being elaborated into a substance which is suitable for subsequent glycosylation. The activation of the saccharide-polyethylene glycol derivative reaction product for glycosylation may occur by manipulation of protecting groups, for example the hydroxyl group may require deprotection, or a protective group may have to be added to make it more active. The choice is dependant on the structure of the product and would be readily apparent to one skilled in the art as to what would be appropriate. The glycosylation is performed under standard liquid-phase chemistry conditions that are well known in the art and are, of course, dependent upon the monosaccharide units and their associated linkages, and upon the nature of protecting groups.

Monitoring of the glycosylation reaction has been found to be easily achieved through nuclear magnetic resonance spectrometry, although other methods could be employed.

The number of additions of glycosylating agent is determined by the amount needed for completion of the reaction, often more than one addition. The glycosylation agent may be any saccharide, and preferably is one having an activated anomeric centre. Despite the repeated additions, it may happen that a small percentage of the glycosyl-accepting hydroxyl may not be completely glycosylated. The hydroxyl should be rendered unreactive by capping with a reagent more reactive than the glycosyl donor. Allyl trichloroacetimidate is an example of such a reagent; the allyl group can be easily reduced under a variety of conditions to a propyl group providing permanent protection of the hydroxyl group defined above.

PEG-DOX can be removed at the end of the synthesis by variety of procedures comprising hydrogenolysis using appropriate catalysts well known in the art, such as palladium or Raney nickel. Furthermore, PEG can be removed from the linker using a hydrogenolytic condition while leaving p-methylbenzyl protecting group on the hydroxyl group where previously DOX-PEG was attached. This feature allows the building of an oligosaccharide intermediate using DOX-PEG, and subsequently transforming this oligosaccharide into a glycosylating agent, with which another oligosaccharide bound to DOX-PEG can be glycosylated.

In place of the monomethylether of polyethylene glycol of average MW 5,000, polyethylene glycol of other molecular masses may be employed. As an example, another suitable polymer is PEG of average MW 12,000. Suitable derivatives include any hydroxyl derivative or substituted hydroxyl derivative. These substances must be capable of linkage through ester or ether tethers to the carbohydrate hydroxyl groups.

The precipitation of the solid oligosaccharide-PEG bound product is most effectively carried out in an anhydrous ether solvent, for example diethyl ether or t-butylmethyl ether. Any water present results in a reduced yield of product. To avoid clogging of filtering devices, preferably the filtration should be done under pressure of an inert anhydrous gas such as nitrogen or argon. One such device utilizing a glass frit as the filter is illustrated in the accompanying drawing.

DESCRIPTION OF THE PREFERRED EMBODIMENTS

Figure 1:
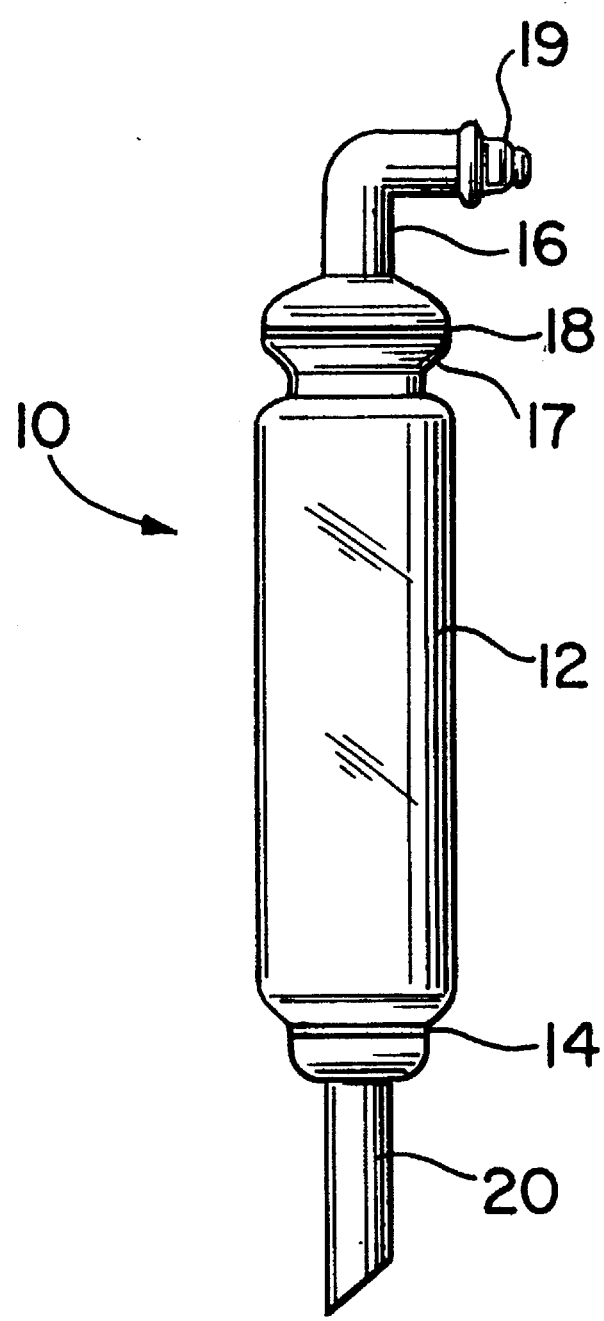
FIG. 1 is a schematic linear view of an apparatus for use as a filter in the practice of the present invention.

In order that the invention may be better understood, preferred embodiments will now be described by way of example only, with reference to the reaction schemes and accompanying drawing.

Referring first to FIG. 1, in its simplest form apparatus 10 consists of a glass cylinder 12 (35 mm external diameter and 23 cm approximate operable length) used vertically so that at the lower end the cylinder 12 is closed by a glass frit 14 (20–50 mesh pore size) and subsequently narrows into a spout 20 (7 cm in length). The cylinder changes at the upper end into a spherical female joint 17 which is operably superimposed upon a male spherical joint 16 in firm abutment together by means of a clip (not shown). Both joints are made air tight by means of a round seal 18 placed between them. The spherical joint 16 ends in a glass tube 19 serving for the attachment of tubing (not shown) for connection with a source of pressurized gas (not shown). In operation, the joint 16 and seal 18 are removed, a slurry containing the precipitated PEG-bound saccharide is placed into the cylinder 12, the seal 18 and the joint 16 are replaced and secured with the clip (not shown), and opened to the pressure of dry pressurized gas. The liquid is forced through the frit 14 under the pressure of the gas whereas the solid is deposited on the surface of the frit 14, from which it can be collected. It is preferred that the filtration under pressure be performed in an apparatus excluding air humidity. Gas pressure is maintained at a suitable level allowing steady flow of the liquid through the frit 14.

In one preferred form of the invention, PEG may be linked to different saccharide hydroxyl groups through ether linkages of Dioxyxylene, DOX. When PEG-DOX is bound to a saccharide hydroxyl, the glycosylation of another saccharide hydroxyl group can be driven to virtual completion by repeated additions of the glycosylating agent. Normally, the use of such an excess of any glycosylating agent in the solution synthesis would create a serious problem for purification; in this procedure the non-polar fragments resulting from the decomposition of the reactants are washed off the precipitated PEG-bound product. The more polar contaminants are removed by simple recrystalilzation of the PEG-bound product from ethanol. Furthermore, since PEG contains a single O—$CH_3$ group ($\delta$=3.380 ppm), the reaction course is easily monitored by NMR spectroscopy using the signal of this methyl as an internal standard.

Glycosylations of PEG-DOX-bound substrates under metal or Lewis acid catalytic conditions well known in the art and comprising the conditions illustrated in the following Examples give good anomeric specificity when glycosylating agents are equipped with a participating group, namely an adjacent functional group that controls the stereochemical outcome of the reaction. Examples of such a participating group comprise ester groups, such as acetyls and benzoyls, and amidic groups such as acetamido and phthalimido groups. PEG-DOX is linked to the acceptor, which is a reactant comprised of at least one monosaccharide with at least one reactive hydroxyl, and, due to the stereochemical control of the glycosylation by the glycosylating agent, the expected anomer is obtained. Glycosylating agents may be added several times, if required for completion of the glycosylation. If glycosylation remains incomplete, capping with an allyl group convertible into a propyl group is executed. Since it is difficult to detect very small amounts of unreacted substrates, it is prudent to include capping after all glycosylation steps. However, if a glycosylation is established to be quantitative, the capping step may be omitted.

After the reaction is completed, the PEG-bound product is precipitated from solution with diether ether, t-butylmethyl ether, or some other ether, filtered, and recrystallized from ethanol, and after drying is ready for the next step of the synthetic sequence. PEG-DOX is cleaved from the requisite saccharide by catalytic hydrogenolysis. Peracetylated oligosaccharides, for final purification, are obtained from dried residues by acetylation with acetic anhydride in pyridine. The purification of the final product is usually achieved by chromatography in its various forms, exemplified by column chromatography, high performance liquid chromatography, or supercritical fluid chromatography. The expected regiospecificity was observed and the expected anomer was formed in each glycosylation; the other anomer was not detected.

The general procedure for handling PEG-bound reactants is that after completion of the reaction, the reaction mixture is filtered to remove any solids present (e.g. molecular sieves), and concentrated to 5–10 mL per gram of PEG. PEG-saccharide is precipitated from this solution after addition of a tenfold excess of t-butylmethyl ether or another ether at 0° C. with vigorous stirring. This precipitate is filtered using the filtering device illustrated in the accompanying drawings under pressure as described for FIG. 1. The precipitation of the solid oligosaccharide-PEG bound product is most effectively carried out in an anhydrous condition; any water present results in a reduced yield of the product. The precipitate can be further purified by recrystallization from absolute ethanol. The precipitate is dissolved in warm absolute ethanol (10–20 mL/g PEG), filtered from any solids, and after cooling, the solid product is collected, rinsed with ethanol and an ether, dried in vacuo, and can be used for the following step. In all other aspects the reaction conditions of reactions performed follow established protocols from classical solution chemistry. Solution chemistry protocols that may be established in the future, and protocols employing enzymes, will be applicable as well.

EXAMPLES

The following examples are used to illustrate the present invention. They should not be construed as limiting it in any way. All parts and percentages are by weight unless otherwise indicated. All abbreviateions and acronyms have the standard meanings in the art. Following these examples is a set of reaction sequences illustrated by structural formulae. These are identified by corresponding numerical references in the sequences and in the written description.

EXAMPLES 1–4

Preparation of Polyethylene Glycol-linker Synthon

EXAMPLE 1

4-(Chloromethyl)phenylmethyl Polyethylene Glycolyl Ether (PEG-DOX-Cl) (Average M.W. 5,000); Exemplified for the Preparation of a Compound of Structural Formula I Dry monomethyl ether of polyethylene glycol (av. m.w. 5,000; 5 g, 1 mmol) was dissolved with heating in anhydrous tetrahydrofuran (THF; 50 mL) with exclusion of humidity and cooled to room temperature. Sodium hydride (0.12 g; 3 mmol) was added with stirring, followed after 10 minutes by sodium iodide (0.17 g, 1.15 mmol) and α,α'-dichloro-p-xylene (5.25 g., 30 mmol). The reaction mixture was stirred for 96 hours. Then another portion of sodium hydride (20 mg) was added followed by iodomethane (100 μL), and the reaction mixture was stirred for 18 hours. Then the reaction mixture was filtered through a celite bed which was subsequently washed with a small amount of dichloromethane (5 mL). The combined filtrate and washings were cooled on an ice-bath, the PEG derivative was precipitated with anhydrous diethyl ether (300 mL). The solid was filtered off and resuspended in ether (100 mL) and filtered again. Then it was redissolved in hot absolute ehtanol (80 mL), cooled to 4° C. until precipitation was completed. After filtration and drying I (5 g; 96%) was obtained. $^1$H NMR (CDCl$_3$); aromatics 7.321 (4H, dd, J 8.33, 14.01, H-3 & H-4); 4.555 (2H, s, OC$\underline{H}_2$C$_6$H$_4$); 4.536 (2H, s, ClC$\underline{H}_2$C$_6$H$_4$); 3.39 (3H, s, C$\underline{H}_3$OPEG).

4-(Chloromethyl)phenylmethyl Polyethylene Glycolyl Ether (Average M.W. 12,000)

The procedure described above was repeated except that monomethylether of polyethylene glycol of average m.w. 12,000 was used and an identical yield of product similar to Ib (97%) was obtained.

EXAMPLE 2

4-(Hydroxymethyl)phenylmethyl Polyethylene Glycolyl Ether (PEG-DOX-OH)(II)

The procedure is exemplified with a specific example of the polymer of av. m.w. 5,000. Exactly the same procedure performed with the polymer of av. m.w. 12,000 gives analogous results.

PEGDOXCl (I, 21.95 g; 4.3 mmol) was dissolved in 10% aqueous Na$_2$CO$_3$ under argon. This solution was heated at 70° C. using an air condenser stoppered with a rubber septum for 16 hrs. The solution was concentrated in vacuo and the residual water removed by co-evaporation with toluene (2×250 mL), and the residue was dried in vacuo. Then the residue was taken up in dichloromethane, filtered, and rinsed three times with dichloromethane (total volume 350 mL). Toluene (100 mL) was added to the filtrate, the solvents were evaporated, and the residue was dried in vacuo. Then the residue was redissolved in dry dichloromethane (75 mL), filtered, and the filtrate was cooled in an ice bath and precipitated with t-butylmethyl ether (900 mL). The precipitate was filtered off, rinsed with t-butylmethyl ether (100 mL) followed by diethyl ether (100 mL) and dried in vacuo. The residue was recrystallized from absolute ehtanol (500 mL), filtered off, rinsed successively with ethanol and t-butylmethyl ether and diethyl ether (100 mL of each) and dried in vacuo as a white powder II (18.2 g; 83%).

EXAMPLE 3

The Determination of Contents of Unreacted Polyethylene Glycol Monomethyl Ether in Preparation of II A preparation of II (100 mg) was dissolved in dry pyridine (2 mL) under an atmosphere of dry argon. To this solution was added acetic anhydride (1 mL) and the reaction sealed and stirred for 16 hrs. Then the solution was cooled in an ice bath and precipitated with t-butylmethyl ether (60 mL). The white solid was filtered off, rinsed with t-butylmethyl ether (30 mL), and dried in vacuo. The ratio of underivatized PEG to PEGDOX was determined by $^1$H NMR comparing two groups of signals (δ, ppm): 4.221 (brt PEG—OCH$_2$C$\underline{H}_2$OAc) and 2.079 (s, PEG—OCH$_2$CH$_2$OCOC$\underline{H}_3$) versus 5.096 (s, C$_6$H$_4$C$\underline{H}_2$OAc) and 4.567 (s, C$\underline{H}_2$OPEG), and 2.099 (s, C$_6$H$_4$CH$_2$OCOC$\underline{H}_3$. Typical values are 1:45–50.

EXAMPLE 4

An Alternate Method for Preparation of II 4-t-Butyldiphenylsilyloxymethyl-hydroxymethyl-benzene (IIIb)

Methyl 4-hydroxymethylbenzoate (5.6 g; 33.7 mmol) was dissolved in dry dichloromethane (75 mL) and imidazole (6.88 g; 0.1 mol) followed by chloro t-butyldiphenylsilane (11.8 mL; 45.5 mmol) were added under an argon atmosphere. The mixture was stirred at room temp. for 1 hr., filtered, rinsed with dichloromethane (50 mL) and the filtrates evaporated. The residue was subjected to chromatography on silica gel eluting with 90:10 hexane-dichloromethane followed by 80:10:10 hexane-ethyl acetate-dichloromethane to yield crude IIIa as a viscous oil: $^1$H NMR (CDCl$_3$): aromatics 8.007 brd(2), 7.68 m(4), 7.40 m(8); methylene 4.813 s(2); t-butyl CH$_3$ 1.105 s(9); ester CH$_3$ 3.910 s(3). $^{13}$C NMR (CDCl$_3$): aromatics PhSi 135.53, 133.25, 127.77, 125.70, Ph 146.34, 129.80, 129.59, 128.81; methylene 65.18; t-butyl CH$_3$ 26.83 C 19.32; ester CO 167.07, CH$_3$ 51.98. After drying in vacuo this oil was dissolved in toluene (150 mL) and cooled to −78° C. under an atmosphere of argon. To this solution was added a 1M THF solution of DIBAL (diisobutylaluminum hydride) (100 mL; 0.1 mol). After 2 hrs. at −78° C. the mixture was poured into ice cold 1M sodium potassium tartrate buffer (500 mL). This mixture was extracted with ethyl acetate (500 mL) and a second extraction (250 mL) was obtained. The organic layer was washed with cold water (2×200 mL), dried with Mg$_2$SO$_4$, filtered and evaporated. The residue was purified on a column of silica gel eluting with hexane-ethyl acetate 70:30, to yield IIIb as a colourless oil (6.1 g; 48% from methyl 4-hydroxymethylbenzoate): $^1$H NMR (CDCl$_3$): aromatics 7.693 m(4), 7.39 brm(10); methylene 4.769 s(2), 4.676 s(2); t-butyl CH$_3$ 1.094 s(9); OH 1.65 s(1). $^{13}$C NMR (CDCl$_3$): aromatics PhSi 135.67, 133.54, 129.69, 127.71, Ph 140.61, 139.52, 126.99, 126.27; methylenes 65.37, 65.28; t-butyl CH$_3$ 26.86 C 19.32. Some unreacted IIIa was recovered from the first fractions.

4-t-butyldiphenylsilyloxymethyl-hydroxymethylbenzene Trichloroacetimidate (IIIc)

Hydroxymethyl silyl ether IIIb (6.1 g; 16.2 mmol) was dissolved in dichloromethane (75 mL) under an atmosphere of dry argon. To this solution was added trichloroacetonitrile (20 mL) and Cs$_2$CO$_3$ (1 g) and the mixture was stirred overnight while sealed with a rubber septum. The reaction mixture was loaded directly onto a silica gel column and eluted with hexane/dichloromethane 90:10 followed by hexane-ethyl acetate-dichloromethane 8:1:1 to yield IIIc as a colourless viscous oil (6.42 g; 76%): $^1$H NMR (CDCl$_3$): NH 8.386 s(1); aromatics 7.68 m(4), 7.40 brm(10); methylenes 5.337 s(2), 4.779 s(2); t-butyl CH$_3$ 1.098 s(9). $^{13}$C NMR (CDCl$_3$): aromatics PhSi 135.57, 133.46, 129.69, 127.73, Ph 141.30, 134.01, 129.71, 126.11; methylene 70.73, 65.27; t-butyl CH$_3$ 26.86 C 19.32, trichloroacetimidate CN 162.67, CCl$_3$ 91.48.

1-Hydroxymethyl-4-(PEGyloxymethyl)benzene PEG-DOX-OH(II)

PEG 5,000 (HOCH$_2$CH$_2$(CH$_2$CH$_2$O)$_n$CH$_3$; av. n=120; 25 g; 5 mmol) previously recrystallized from ethanol and dried in vacuo was added to a mixture of dichloromethane (180 mL), IIIc (6.42 9; 12.3 mmol) and activated 3A molecular sieves (1 g). This mixture was cooled in an ice bath with stirring under an atmosphere of argon and after about 20 mins., BF$_3$.OEt$_2$ (1.08 mL, 8.75 mmol) was added dropwise. After 4 hrs. diisopropylethylamine (1.5 mL) was added. Then the molecular sieves were removed by filtration, and rinsed with dichloromethane (50 mL). The filtrates were concentrated to about 150 mL, cooled in an ice bath and precipitated with t-butylmethyl ether (1 L). The precipitate was isolated by filtration, rinsed with t-butylmethyl ether (100 mL) and then recrystallized from absolute ethanol (1 L). The precipitate was filtered by suction, rinsed with ethanol (100 mL) and t-butylmethylether (100 mL) and dried in vacuo to yield crude IIId: $^1$H NMR (CDCl$_3$): aromatics 7.69 m(4), 7.38 brm(10); methylene 4.760 s(2), 4.559 s(2); t-butyl CH$_3$ 1.084 s(9); PEG CH$_3$ 3.379 s(3). To IIId was added tetrahydrofuran (160 mL) followed by tetrabutylammonium fluoride (1M in tetrahydrofuran, 10 mL; 10 mmol) under argon. The reaction mixture was heated at 50° C. stoppered with a septum and a balloon of dry argon for 16 hrs. The solution was then concentrated and residual water was removed by co-evaporation with toluene (2×100 mL) followed by drying in vacuo. The residue was then recrystallized twice from absolute ethanol and the precipitate rinsed each time with ethanol (2×100 mL) and t-butylmethylether (100 mL) and finally dried in vacuo to yield II as a white powder (11.75 g; 46%). $^1$H NMR (CDCl$_3$): aromatics 7.335 s(4); methylenes 4.671 d(2) J 4.2, 4.558 s(2); PEG OCH$_3$ 3.377 s(3); OH 2.7 brt (1).

EXAMPLES 5 & 6

Preparation of an Oligosaccharide Using PEG-DOX Attached to the Anomeric Carbon

EXAMPLE 5

Preparation of PEG-DOX-pentasaccharide [Man(α1–2)]$_4$Man IXa

PEG-DOXyl 2-O-acetyl-3,4,6-tri-O-benzyl-α-D-mannopyranoside (Va)

Dichloromethane (15 mL) was added to a mixture of PEGDOXOH (II, 4.0 g, 0.78 mmol) and 4A molecular sieves (1 g) followed by a solution of 2-O-acetyl-3,4,6-tri-O-benzyl-α-D-mannopyranosyl trichloroacetimidate IV (875 mg, 1.36 mmol) in dichloromethane (5 mL) under an atmosphere of argon with stirring. This mixture was cooled in an ice bath and after 30 mins. triethylsilyl trifluoromethanesulfonate (TESOTf)(177 μL, 0.78 mmol) was added by syringe. After 4 hrs. at this temperature, diisopropylethylamine (10 drops, about 90 mg) was added to the solution and after 5 min. excess t-butylmethyl ether (230 mL) was added to precipitate the polymer. The white solid was separated by filtration and after rinsing with t-butylmethyl ether (50 mL) was recrystallized from absolute ethanol (200 mL). The white precipitate was collected by filtration and after rinsing with ethanol and t-butyl methylether (50 mL each) was dried in vacuo to yield Va (4.11 g, 92%). $^1$H NMR (CDCl$_3$): aromatics 7.40–7.25 m(17); 7.150 dd J=7.6 and 2.0 (2); 5.408 dd, J$_{12}$ 1.8 and J$_{23}$ 3.3; H-2$_a$, 4.924 d H-1$_a$; methylenes 4.849 d(1) J$_{HH}$ 10.8, 4.72–4.66 m(2), 4.58–4.48 m(7); PEG CH$_3$ 3.382 s(3); acetate CH$_3$ 2.137 s(3).

PEG-DOXyl 3,4,6-tri-O-benzyl-α-D-mannopyranoside (Vb)

Polymer bound monosaccharide Va (4.11 g, 0.72 mmol) was dissolved in dry methanol (20 ml) by gentle heating with a heat gun. After cooling to room temperture, 1,8-diazabicyclo[5.4.0]undec-7-ene (DBU; 12 drops from a Pasteur pipette, about 200 mg) was added and the solution stirred tightly stoppered for 16 hrs. The solution was cooled in an ice bath and the polymer was precipitated by the addition of t-butyl methylether (350 mL). The solid was recovered by filtration and after rinsing with t-butylmethyl ether it was recrystallized from absolute ethanol (250 mL). The white solid was collected by filtration and after rinsing with ethanol and t-butylmethyl ether (50 mL each) was dried in vacuo to yield alcohol Vb (3.83 g, 97%). $^1$H NMR (CDCl$_3$): aromatics 7.35–7.25 m(17); 7.148 dd J$_{HH}$ 7.6 and 1.8 (2); 4.956 d $J_{12}$ 1.3 H-$1_a$; 4.040 m H-$2_a$; methylenes 4.798 d(1) $J_{HH}$ 10.6, 4.70–4.62 m(4), 4.55–4.44 m(5); PEG CH$_3$ 3.382; hydroxyl 2.431 d $J_{2OH}$ 2.6.

PEG-DOXyl 2-O-(2-O-acetyl-3,4,6-tri-O-benzyl-α-D-mannopyranosyl)-3,4,6-tri-O-benzyl-α-D-mannopyranoside (VIa)

In a manner analogous to the preparation of Va, VIa (3.97 g, 93%) was prepared. $^1$H NMR (CDCl$_3$): aromatics 7.40–7.1 m(34); 5.536 dd $J_{12}$ 1.7 and $J_{23}$ 3.1 H-$2_b$; 5.067 d H-$1_b$; 4.977 d H-$1_a$; methylenes 4.9–4.3 m(16); PEG CH$_3$ 3.382 s(3); acetate CH$_3$ 2.113 s(3).

PEG-DOXyl 3,4,6-tri-O-benzyl-2-O-(3,4,6-tri-O-benzyl-α-D-mannopyranosyl-α-D-mannopyranoside (VIb)

Polymer bound disaccharide VIa was deacetylated as described for the preparation of Vb to yield disaccharide alcohol VIb (3.93 g, 99%. $^1$H NMR (CDCl$_3$): aromatics 7.40–7.10 m(34); 5.134 d $J_{12}$ 1.7 H-$1_b$; 5.019 d $J_{12}$ 2.0 H-$1_a$; 4.125 m H-$2_b$; 4.067 m H-$2_a$; methylenes 4.85–4.30 m (16); PEG CH$_3$ 3.382; hydroxyl 2.396 d $J_{2OH}$ 2.4.

PEG-DOXyl 2-O-[(2-O-acetyl-3,4,6-tri-O-benzyl-α-D-mannopyranosyl)-2-O-(3,4,6-tri-O-benzyl-α-D-mannopyranosyl)]-3,4,6-tri-O-benzyl-α-D-mannopyranoside (VIIa)

Prepared as it is described for Va, VIIa was obtained (3.92 g, 91%). $^1$H NMR (CDCl$_3$): aromatics 7.40–7.1 m(49); 5.531 dd $J_{12}$ 1.6 and $J_{23}$ 3.1 H-$2_c$; 5.185 d H-$1_c$ $J_{12}$ 1.6; 5.041 d H-$1_b$ $J_{12}$ 1.8; 5.015 d H-$1_a$ $J_{12}$ 1.8; 4.091 m H-$2_b$; 4.012 m H-$2_a$; methylenes 4.86–4.3 m(22); PEG CH$_3$ 3.382 s(3); acetate CH$_3$ 2.122 s(3).

PEG-DOXyl 3,4,6-tri-O-benzyl-2-O-[(3,4,6-tri-O-benzyl-α-D-mannopyranosyl)-2-O-(3,4,6-tri-O-benzyl-α-D-mannopyranosyl)]-α-D-mannopyranoside (VIIb)

Polymer bound trisaccharide VIIa was deacetylated as described for the preparation of Vb to yield trisaccharide alcohol VIIb (not shown in the Schemes)(3.70 g, 95%). $^1$H NMR (CDCl$_3$): aromatics 7.35–7.10 m(49); 5.215 d $J_{12}$ 1.7 H-$1_c$; 5.114 d $J_{12}$ 1.7 H-$1_b$; 5.034 d $J_{12}$ 2.0 H-$1_a$; 4.109 m H-$2_b$+H-$2_c$; 4.009 m H-$2_a$; methylene 4.82–4.26 m(22); PEG CH$_3$ 3.382; hydroxyl 2.363 d $J_{2OH}$ 2.6.

PEG-DOXyl 2-O-[(2-O-acetyl-3,4,6-tri-O-benzyl-α-D-mannopyranosyl)-2-O-(3,4,6-tri-O-benzyl-α-D-mannopyranosyl)-2-O-(3,4,6-tri-O-benzyl-α-D-mannopyranosyl)]-3,4,6-tri-O-benzyl-α-D-mannopyranoside VIIIa Prepared as it is described for Va, VIIIa was obtained (3.72 g, 92%). $^1$H NMR (CDCl$_3$): aromatics 7.40–7.0 m(64); 5.545 dd $J_{12}$ 1.7 and $J_{23}$ 3.1 H-$2_d$; 5.218 d 1.7 H-$1_d$; 5.171 d $J_{12}$ 1.7, H-$1_c$; 5.051 d $J_{12}$ 1.7 H-$1_b$; 5.027 d $J_{12}$ 1.8 H-$1_a$; 4.081 m H-$2_b$+H-$2_c$; 4.001 m H-$2_a$; methylenes 4.86–4.12 m(28); PEG CH$_3$ 3.382 s(3); acetate CH$_3$ 2.119 s(3).

PEG-DOXyl 3,4,6-tri-O-benzyl-2-O-[(3,4,6-tri-O-benzyl-α-D-mannopyranosyl)-2-O-(3,4,6-tri-O-benzyl-α-D-mannopyranosyl)-2-O-(3,4,6-tri-O-benzyl-α-D-mannopyranosyl)]-α-D-mannopyranoside (VIIIb)

Polymer bound tetrasaccharide VIIIa was deacetylated as it is described for the preparation of Vb to yield tetrasaccharide alcohol VIIIb (not shown in Schemes)(3.65, 98%). $^1$H NMR (CDCl$_3$): aromatics 7.40–7.0 m(64); 5.224 d 1.7 H-$1_d$, 5.205 d $J_{12}$ 1.7, H-$1_c$; 5.107 d $J_{12}$ 1.7 H-$1_b$; 5.055 d $J_{12}$ 1.7 H-$1_a$; PEG CH$_3$ 3.382 s(3); hydroxyl 2.361 d $J_{2OH}$ 2.7

PEG-DOXyl 2-O-[(2-O-acetyl-3,4,6-tri-O-benzyl-α-D-mannopyranosyl)-2-O-(3,4,6-tri-O-benzyl-α-D-mannopyranosyl)-2-O-(3,4,6-tri-O-benzyl-α-D-mannopyranosyl)-2-O-(3,4,6-tri-O-benzyl-α-D-mannopyranosyl)]-3,4,6-tri-O-benzyl-α-D-mannopyranoside (IXa)

Prepared as it is described for Va, IXa was obtained (3.85 g, 97%), $^1$H NMR (CDCl$_3$): aromatics 7.40–6.95 m(79); 5.540 m H-$2_a$; 5.240 s H-$1_d$; 5.225 s H-$1_d$; 5.114 s H-$1_c$; 5.072 s H-$1_b$; 5.027 s H-$1_a$; PEG CH$_3$ 3.380 s(3); acetate CH$_3$ 2.116 s(3).

EXAMPLE 6

Preparation of Gal(β1–2)Man(α1–6)Glc(α/β)PEG-DOX

PEG-DOXyl 6-O-acetyl-2,3,4,-tri-O-benzyl-α/β-D-glucopyranoside (XIa)

Dichloromethane (4 mL) was added to a mixture of PEGDOX-OH (1.25 g, 0.24 mmol) and 4A molecular sieves (about 300 mg) followed by a solution of ethyl 6-O-acetyl-2,3,4-tri-O-benzyl-α/β-D-thioglucopyranoside X (286 mg, 0.48 mmol) in dichloromethane (4 mL) under an atmosphere of argon with stirring. This mixture was cooled in an ice bath and after 30 mins. methyl trifluormethanesulfonate (46 μL, 0.36 mmol) was added. The temperature was allowed to rise to room temp., and after 16 hrs. diisopropylethylamine (5 drops, about 45 mg) was added to the solution, followed after 5 min. with an excess of t-butylmethyl ether (90 mL) to precipitate the polymer. The white solid was separated by filtration and after rinsing with t-butylmethyl ether (50 mL) it was recrystallized from absolute ethanol (80 mL). The white precipitate was collected by filtration and after rinsing with ethanol and with t-butylmethyl ether (25 mL each) it was dried in vacuo to yield XIa (1.18 g, 86%). $^1$H NMR (CDCl$_3$): aromatics 7.40–7.20 m(19); 4.815 d $J_{12}$ 2.9 H-$1_a$; 4.267 dd $J_{56}$ 4.4 H-$6_a$α; 4.174 dd $J_{56'}$ 2.2 $J_{66'}$ –12.1 H-$6'_a$α; 4.058 t $J_{23}$ 9.2 $J_{34}$ 9.2 H-$3_a$α; 3.863 ddd H-$5_a$α; methylene 5.019 d(1) J 10.7; PEG CH$_3$ 3.382 s(3); acetate CH$_3$ 2.058β, 2.030αs(3); α:β 2.8:1.

PEG-DOXyl 2,3,4-tri-O-benzyl-α/β-D-glucopyranoside (XIb)

Polymer bound monosaccharide XIa (1.18 g, 0.21 mmol) was dissolved in dry methanol (12 mL) by gentle heating with a heat gun. After cooling to room temperature, 1,8-diazabicylco[5.4.0]undec-7-ene (DBU, 6 drops from a Pasteur pipette, about 100 mg) was added and the solution stirred closed for 16 hrs. The solution was cooled in an ice bath and the polymer was precipitated by the addition of t-butylmethyl ether (90 mL). The solid was recovered by filtration and after rinsing with t-butylmethyl ether was recrystallized from absolute ethanol (80 mL). The white solid was collected by filtration and after rinsing with ethanol and t-butylmethyl ether (25 mL each) and drying in vacuo XIb was obtained (1.17 g, 99%). $^1$H NMR (CDCl$_3$): aromatics 7.40–7.20 m(19); 4.799 d $J_{12}$ 3.7 H-1$_a\alpha$; 4.058 t $J_{23}$ 9.5 $J_{34}$ 9.5 H-3$_a\alpha$; methylene 5.004 d(1) J 10.8; PEG CH$_3$ 3.382 s(3).

PEG-DOXyl 6-O-(2-O-acetyl-3,4,6-tri-O-benzyl-α-D-mannopyranosyl)-2,3,4-tri-O-benzyl-α/β-D-glucopyranoside (XIIa)

Prepared as for Va using donor IV, acceptor XIb, and TESOTf as promoter yielded in 2 hrs. reaction XIIa (1.17 g, 90%). $^1$H NMR (CDCl$_3$): aromatics 7.40–7.10 m(34); 4.909 d $J_{12}$ 1.8 H-1$_b$; 4.777 d $J_{12}$ 3.3 H-1$_a\alpha$; 5.402 dd $J_{23}$ 3.3 H-2$_b$; methylene 5.004 d(1) J 10.8; PEG CH$_3$ 3.382 s(3); acetate CH$_3$ 2.143α, 2.137β.

PEG-DOXyl 6-O-(3,4,6-tri-O-benzyl-α-D-mannopyranosyl)-2,3,4-tri-O-benzyl-α-D-glucopyranoside (XIIb)

Compound XIIa was deacetylated as in the preparation of XIb, and XIIb was obtained (1.07 g, 90%). $^1$H NMR (CDCl$_3$): aromatics 7.40–7.10 m(34); 4.961 d $J_{12}$ 1.7 H-1$_b$; 4.783 d $J_{12}$ 4.0 H-1$_a\alpha$; PEG CH$_3$ 3.382 s(3); hydroxyl 2.443 d $J_{2OH}$ 2.9.

PEG-DOXyl 6-O-[2,3,4,6 tetra-O-acetyl-β-D-galactopyranosyl-2-O-(3,4,6-tri-O-benzyl-α-D-mannopyranosyl)]-2,3,4-tri-O-benzyl-α-D-glucopyranoside (XIVa)

Alcohol XIIb (1.07 g, 0.17 mmol) was glycosylated with 2,3,4,6-tetra-O-acetyl-galactopyranosyl trichloracetimidate XIII (167 mg, 0.34 mmol) in dichloromethane (6 mL) at 0°–5° C. for 4 hrs. using trifluoromethanesulfonic anhydride (29 μL, 0.17 mmol) as promoter to give polymer bound trisaccharide XIVa (806 mg, 72%). $^1$H NMR (CDCl$_3$): PEG CH$_3$ 3.382 s(3); acetates CH$_3$ 2.160, 2.013, 1.990, 1.989 4×s(3).

EXAMPLES 7 & 8

Removal of Polymer-linker After Completion of Synthesis from the Anomeric Hydroxyl

EXAMPLE 7

1,3,4,6-Tetra-O-acetyl-2-O-(2,3,4,6-tetra-O-acetyl-α-D-mannopyranosyl)-α/β-D-mannopyranose (VIc)

Procedure A. To PEG-DOX bound disaccharide VIa (1.10 g, 0.18 mmol) was added Raney Ni W-2 (Aldrich 50% aqueous slurry, 5 g). Before use, the catalyst was washed with water until neutral with pH paper (3×), then with ethanol (3×) and without allowing it to dry added as an ethanol slurry to the reaction flask (approximately 50 mL of ethanol total) and the reaction mixture was refluxed under argon for 4 hrs. The hot solution was filtered through a celite bed and rinsed well with warm ethanol (100 mL). Toluene (35 mL) was added to the combined filtrate and washings, concentrated to a volume of about 40 mL. After cooling on ice, the precipitated PEG was removed by filtration, rinsed with ethanol (50 mL) and the combined filtrate and washings were evaporated to dryness. The residue was acetylated and purified as described in the following paragraph to yield VIc (58 mg, 36%).

Procedure B. PEG-DOX bound disaccharide VIa (1.19 g, 0.19 mmol) dissolved in acetic acid:water (1:1, 30 mL) was hydrogenated along with palladium black (450 mg) in a pressure bottle with a Parr hydrogenation apparatus at 50 p.s.i. at room temperature for 16 hrs. The catalyst was removed by filtration through a celite bed and rinsed well with methanol:water 9:1. The combined filtrates were evaporated at high vacuum (water bath temp. 40°–45° C.). The residue was co-evaporated with toluene (50 mL) and dried in vacuo. The solids were recrystallized from ethanol (100 mL) and collected by filtration; then rinsed with ethanol (25 mL) and t-butylmethyl ether (25 mL). The combined filtrate and washings were evaporated and rehydrogenated in 95% ethanol (30 mL) using palladium black (250 mg) as above. The catalyst was removed by filtration through a celite bed, rinsed well with 95% ethanol, and the combined filtrate and washings were concentrated at high vacuum. The residue was dissolved in pyridine (5 mL), cooled in an ice bath under an atmosphere of argon and acetic anhydride (2.5 mL) was added to the mixture. After stirring for 16 hrs. and allowing to warm to room temperature the solvents were removed by evaporation at high vacuum. The residue was chromatographed on a silica gel column eluting with 2% methanol in dichloromethane to yield VIc (25 mg). $^1$H NMR (CDCl$_3$): 6.246 d $J_{12}$ 2.0 H-1$_a\alpha$; 4.050 dd $J_{23}$ 3.2 H-2$_a\alpha$; 5.297 dd $J_{34}$ 10.7 H-3$_a\alpha$; 5.434 dd $J_{45}$ 10.0 H-4$_a\alpha$; 4.18 m H-5$_a\alpha$; 4.238 dd $J_{56}$ 4.1 H-6$_a\alpha$; 4.131 dd $J_{56'}$ 2.4 $J_{66'}$ –12.4 H-6'$_a\alpha$; 4.950 d $J_{12}$ 1.6 H-1$_b$; 5.284 m $J_{23}$ 4.3 H-2$_b$; 5.403 dd $J_{34}$ 7.9 H-3$_b$; 5.278 dd $J_{45}$ 7.9 H-4$_b$; 4.051 ddd $J_{56}$ 2.6 H-5$_b$; 4.22 m $J_{56'}$ 2.7 H-6+6'$_b$; acetates 2.155 s(6); 2.143 s(3); 2.105 s(3); 2.089 s(3); 2.047 s(6); 2.012 s(3). $^{13}$C NMR (CDCl$_3$): acetates C=O 170.9, 170.7, 170.5, 169.9, 169.7, 169.4, 169.2, 168.2; CH$_3$ 20.9, 20.6; 99.28 C-1$_b$; 91.50 C-1$_a$; 75.90, 70.75, 69.88, 69.71(2), 68.36, 66.26, 65.54, 62.45, 61.77 C-2-C-6$_{a+b}$.

1,3,4,6-Tetra-O-acetyl-2-O-[2-O-(2,3,4,6-tetra-O-acetyl-α-D-mannopyranosyl)-2-O-(3,4,6-tri-O-acetyl-α-D-mannopyranosyl)-2-O-(3,4,6-tri-O-acetyl-α-D-mannopyranosyl)-2-O-(3,4,6-tri-O-acetyl-α-D-mannopyranosyl)]-α/β-D-mannopyranose (IXb)

Polymer bound pentasaccharide IXa was treated using Procedure A for the preparation of disaccharide VIc except that 95% ethanol at reflux for 16 hours was used and the PEG was not removed by crystallization from ethanol until after acetylation. The evaporated filtrate was purified on a column of silica gel eluting with 5% methanol in dichloromethane/toluene (1:1). Mass spectral analyses of this fraction showed peaks for Ac$_4$Hex$^+$ 331, Ac$_7$Hex$_2^+$ 619, Ac$_{10}$Hex$_3^+$ 907, Ac$_{13}$Hex$_4^+$ 1195 as expected for a linear acetylated pentasaccharide. However peaks at Ac$_{15}$BnHex$_5^+$ 1531, Ac$_{14}$Bn$_2$Hex$_5^+$ 1579, Ac$_{13}$Bn$_3$Hex$_5^+$ 1627 and Ac$_{15}$BnHex$_5$—BnCH$_3^-$NH$_4$+ 1670 as well as a series of peaks at Ac$_3$BnHex$^+$ 379, Ac$_7$BnHex$_2^+$ 667, Ac$_{10}$BnHex$_3^+$ 955, Ac$_{13}$BnHex$_4^+$ 1243 and Ac$_{13}$BnHex$_4^+$ 1291 indicated the presence of uncleaved benzyl groups. This mixture was retreated with Raney Ni W-2 for 16 hrs. at reflux and reacetylated as above to give IXb: Mass spectrum Ac$_4$Hex$^+$ 331, Ac$_7$Hex$_2^+$ 619, Ac$_{10}$Hex$_3^+$ 907, Ac$_{13}$Hex$_4^+$ 1195, Ac$_{16}$Hex$_5^+$ 1484, MNa$^+$ 1566. $^1$H NMR (CDCl$_3$) 6.259 d $J_{12}$ 2.2 H-1$_a$, 5.175 d $J_{12}$ 1.8 H-1$_b$, 5.119 m H-1$_{c+d}$; 4.973 s $J_{12}$H-1$_c$; 5.297 m h-2$_c$; 4.077 m H-2$_a$. $^{13}$C NMR (CDCl$_3$) 91.71 C-1$_a$, 100.08, 99.63, 99.48, 99.38 C-1$_{b-c}$.

2-O-[2-O-(α-D-mannopyranosyl)]-2-O-(α-D-mannopyranosyl)-2-O-(-α-D-mannopyranosyl)-2-O-(-α-D-mannopyranosyl)-α/β-mannopyranose (IXd)

A small specimen of IXb was deacetylated using 0.05M sodium methoxide in methanol for 18 hours at room temperature. After neutralization with mixed bed resin, filtration and evaporation to dryness, compound IXd was obtained. $^1$H NMR (CDCl$_3$): 5.216 1H H-1$_b$, 5.142 1H H-1$_c$, 5.130 2H H-1$_{c,d}$, 4.880 H-1$_{a\alpha}$, 4.498 H-1$_{a\beta}$. Mass spectrum: MH$^+$ 829, MNa$^+$ 851.

EXAMPLE 8

6-O-[2,3,4,6 tetra-O-acetyl-β-D-galactopyranosyl-2-O-(3,4,6-tri-O-acetyl-α-D-mannopyranosyl)]-1,2,3,4-tetra-O-acetyl-α/β-D-glucopyranose (XIVb)

Polymer bound trisaccharide XIVa (396 mg, 0.06 mmol) was hydrogenated at 50 p.s.i. and 50° C. for 16 hrs in acetic acid:water 1:1 in the presence of palladium black (125 mg). The catalyst was removed by filtration through a celite bed and rinsed well with methanol:water 9:1 (50 mL). The filtrate and washings were evaporated to dryness, followed by co-evaporation with toluene (25 mL), and then acetylated with pyridine (5 mL) and acetic anhydride (2.5 mL). The peracetylated trisaccharide was isolated by evaporation of the solvents followed by chromatography on silica gel eluting with 3% methanol in dichloromethane to yield XIVb (16 mg, 28%), which after chromatography gave mass spectrum: Ac$_4$Hex$^+$ 331, Ac$_7$Hex$_2$$^+$ 619, Ac$_{10}$Hex$_3$$^+$ 907, MH$^+$ 967, MNH$_4$$^+$ 984, and $^1$H NMR (CDCl$_3$): 6.321 d J$_{12}$ 3.7 H-1$_a$α; 5.698 d J$_{12}$ 8.1 H-1$_a$β (α:β 2.7:1); 4.711 d J$_{12}$ 1.0 H-1$_b$α; 4.781 d J$_{12}$ 1.1 H-1$_b$β; 4.372 J$_{12}$ 8.0 H-1$_c$.

EXAMPLE 9

Preparation of an Oligosaccharide Using PEG-DOX Attached to a Ring Carbon (Lactosamine Synthesis)

Allyl 2-acetamido-4,6-O-benzylidene-2-deoxy-3-O-PEGDOXyl-β-D-glucopyranoside (XVb)

Allyl 2-acetamido-4,6-O-benzylidene-2-deoxy-β-D-glucopyranoside (XVa, 720 mg, 2.0 mmol) was dissolved in THF (50 mL) at 50° C. under an atmosphere of argon. To this solution was added NaH (60% dispersion in oil, 152 mg, 4 mmol) and after stirring for 30 minutes PEG-DOXCl (5.1 g, 1 mmol) and NaI (225 mg, 1.5 mmol) were added as solids. The flask was stoppered tightly and the stirring at 50° C. was continued for 48 hrs. Then solid ammonium chloride (214 mg, 4 mmol) was added, and after 5 mins. the mixture was filtered and the filtrate concentrated to dryness. The residue was taken up in dichloromethane (3×50 mL), filtered and evaporated to dryness. This residue was taken up in dry dichloromethane (50 mL), filtered quickly and under an atmosphere of argon cooled in an ice-bath, and precipitated with t-butylmethyl ether (500 mL). The solids were collected by filtration and recrystallized from ethanol (250 mL) to yield XVb (4.93 g, 90%). $^1$H NMR (CDCl$_3$): aromatics 7.493 brd(2) J 6.4, 7.35 m(7); 5.556 s PhCH; 4.796 d J$_{12}$ 8.3 H-1, 5.91 m NH; methylene 4.575 q(2) J 11.1; allyl 5.915 m(1), 5.316 m(1), 5.226 m(1), 4.352 ddd(2); PEG CH$_3$ 3.382 s(3); acetate CH$_3$ 2.051.

Allyl 4,6-O-benzylidene-2-deoxy-3-O-PEGDOXyl-2-phthalimido-β-D-glucopyranoside (XVd)

Polymer bound sugar XVd was prepared from allyl 4,6-O-benzylidene-2-deoxy-2-phthalimido-β-D-glucopyranoside (XVc, 765 mg, 1.75 mmol) according to the procedure for XVb yielding (3.95 g, 82%). $^1$H NMR (CDCl$_3$): aromatics 7.9–7.7 m(4) Phth, 7.5 m and 7.41–7.22 m(6), 7.091 brd(2) J 10.8, 6.960 and 6.859 2×d(2) J$_{HH}$ 8.1 DOX; 5.623 s PhCH; 5.233 d J$_{12}$ 8.7 H-1; methylenes 4.775 q(2), 4.561 s(2); allyl 5.654 m(1), 5.101 m(1), 5.007 m(1); PEG CH$_3$ 3.382 s(3).

Allyl 2-acetamido-2-deoxy-3-O-PEGDOXyl-β-D-glucopyranoside (XVe)

Prepared as described below for XVf from ether XVd, XVb (4.93 g, 0.90 mmol) yielded diol XVe (4.87 g, 98%). $^1$H NMR (CDCl$_3$): aromatics 7.330 brs(4) DOX; 4.896 d J$_{12}$ 8.2 H-1, 5.975 d J$_{2NH}$ 7.5 NH; methylene 4.756 s(2), 4.538 s(2); allyl 5.879 m(1), 5.263 m(1), 5.169 m(1); PEG CH$_3$ 3.382 s(3); acetate 1.946 s(3).

Allyl 2-deoxy-3-O-PEGDOXyl-2-phthalimido-β-D-glucopyranoside (XVf)

The benzylidene group of 3-O-PEGDOXyl ether XVd (3.94 g, 0.71 mmol) was cleaved by heating at 100° C. for 40 mins. in 60% aqueous acetic acid (40 mL). The solvents were removed by evaporation and subsequent co-evaporation with toluene (50 mL). The product was then obtained by recrystallization from ethanol to yield diol XVf (3.74 g, 96%). $^1$H NMR (CDCl$_3$): Aromatics 7.85–7.65 m(4) Phth, 7.338 brs(2) DOX, 7.034 and 6.972 2×d(1) J$_{HH}$ 8.1 DOX; 5.197 d J$_{12}$ 8.3 H-1; methylenes 4.560 s(2), 4.315 s(2); allyl 5.671 m(1), 5.091 m(1), 5.011 m(1); PEG CH$_3$ 3.382 s(3).

Allyl 2-acetamido-2-deoxy-6-O-(t-butyldiphenylsilyl)-3-O-PEGDOXyl-β-D-glucopyranoside (XVg)

Diol XVe (4.87 g, 0.88 mmol) was dissolved in dichloromethane (10 mL) and imidazole (204 mg, 3.0 mmol) was added as a solid followed by chloro-t-butyldiphenylsilane (390 μL, 1.5 mmol) by syringe under an atmosphere of argon. The mixture was tightly stoppered and stirred for 16 hrs. Then the mixture was cooled in an ice bath and precipitated with t-butylmethyl ether (150 mL) and after collection by filtration was recrystallized twice from ethanol (150 mL) to yield alcohol XVg (4.72 g, 91%). $^1$H NMR (CDCl$_3$): aromatics 7.330 brs(4) DOX; 4.883 d J$_{12}$ 8.2 H-1, 5.574 d J$_{2NH}$ 7.7 NH; methylenes 4.823, 4.709 2×d J$_{HH}$ 11.7, 4.554 s(2); allyl 5.857 m(1), 5.228 m(1), 5.149 m(1); PEG CH$_3$ 3.382 s(3); acetate 1.870 s(3); t-butyl 1.060 s(9) CH$_3$.

Allyl 2-deoxy-6-O-(t-butyldiphenylsilyl)-3-O-PEG-DOXyl-2-phthalimido-β-D-glucopyranoside (XVh)

Silyl ether XVh was prepared, as described above for the synthesis of XVg, from diol XVf (3.74 g, 0.64 mmol). The compound XVh (3.83 g, 93%) had $^1$H NMR (CDCl$_3$): aromatics 7.704 m, 7.42 m, 7.313 s, 7.036 and 6.938 2×d(1) J$_{HH}$ 8.0 DOX; 5.170 d J$_{12}$ 8.2 H-1; methylenes 4.560 s(2), 4.317 s(2); allyl 5.656 m(1), 5.057 m(1), 4.989 m(1); PEG CH$_3$ 3.382 s(3); t-butyl 1.086 s(9) CH$_3$.

Allyl 4-O-(2,3,4,6-tetra-O-acetyl-β-D-galactopyranosyl)-2-deoxy-6-O-(t-butyldiphenylsilyl)-3-O-PEG-DOXyl-2-phthalimido-β-D-glucopyranoside (XVIa)

Alcohol XVh (0.55 g, 0.10 mmol) was glycosylated with 2,3,4,6-tetra-O-acetyl-galactopyranosyl trichloracetimidate XIII (98 mg, 0.20 mmol) in dichloromethane (5 mL) in the presence of activated molecular sieves 3A (500 mg) at 0°–5° C. for 2 hrs. using trifluoromethanesulfonic anhydride (25 μL, 0.15 mmol) as promoter to give after workup by precipitation with t-butylmethyl ether and recrystallization from ethanol the polymer-bound disaccharide XVIa (512 mg, 88%. $^1$H NMR (CDCl$_3$): aromatics 7.010 and 6.854

2×d(1) $J_{HH}$ 7.7 DOX; 5.323 d $J_{34}$ 3.1 H-4$_b$; methylenes 4.819 and 4.474 2×d(1) $J_{HH}$ 12.2, 4.560 s(2); allyl 5.715 m(1); PEG CH$_3$ 3.382 s(3); acetates 2.046, 2.004 and 1.868 4×s(3) CH$_3$; t-butyl 1.086 s(9) CH$_3$.

EXAMPLE 10

Removal of Polymer-linker After Completion of Synthesis from a Non Anomeric Hydroxyl Propyl 4-O-(2,3,4,6-tetra-β-D-galactopyranosyl)-2-deoxy-6-O-(t-butyldiphenylsilyl)-2-phthalimido-β-D-glucopyranoside (XVIb)

Polymer bound disaccharide XVIa (512 mg, 0.089 mmol) was hydrogenated in acetic acid:water 1:1 in the presence of palladium black (175 mg) for 16 hrs. at room temperature and 50 p.s.i. of H$_2$. The catalyst was removed by filtration through a celite bed and rinsed with water and methanol. After evaporation of the solvent and chromatography, the disaccharide derivative XVIb was obtained and characterized by its mass spectrum: Ac$_4$Hex$^+$ 331, M—C$_3$H$_7$O$^+$ 861, MH$^+$ 923, MNH$_4$$^+$ 938.

Propyl 4-O-(2,3,4,6-tetra-O-acetyl-β-D-galactopyranosyl)-2-acetamido-3,6-di-O-acetyl-2-deoxy-β-D-glucopyranoside (XVId)

Polymer bound disaccharide XVIa (400 mg, 0.045 mmol) was treated with hydrazine hydrate (5 mL) and ethanol (10 mL) for 2 hrs. at 75° C. under an atmosphere of argon. The liquids were removed by evaporation at high vacuum and the residue was acetylated by cooling in an ice bath and adding pyridine (10 mL) followed by acetic anhydride (5 mL) and stirring at room temperature overnight. The liquids were removed by evaporation at high vacuum and the dry residue was dissolved in dichloromethane (5 mL) and precipitated with t-butylmethyl ether (150 mL). After collection by filtration the solids were recrystallized from ethanol (60 mL). The resulting solid (344 mg) was dissolved in tetrahydrofuran (7 mL) and 1M tetrabutylammonium fluoride in tetrahydrofuran (200 μL) and heated at 50° C. in a stoppered flask for 16 hrs. After evaporation of the liquids and drying in vacuo, the residue was dissolved in dichloromethane, precipitated with t-butylmethyl ether and recrystallized from ethanol as above. The resulting dry solid (329 mg) was hydrogenated in acetic acid:water 1:1 as described above for XVIb and then acetylated and purified by chromatography on a short silica gel column. Elution with dichloromethane:methanol 25:1, and filtration through an LH-20 Sephadex column (to remove a small amount of monosaccharide impurity) using chloroform:methanol 4:3 yielded known peracetylated disaccharide XVc (12 mg, 39%) showing mass spectrum: Ac$_4$Hex$^+$ 331, M—C$_3$H$_7$O$^+$ 618, MH$^+$ 678, and $^1$H NMR (CDCl$_3$): 4.501 d $J_{12}$ 8.0 H-1$_b$, 5.082 dd $J_{23}$ 10.4 H-2$_b$, 4.979 dd $J_{34}$ 3.5 H-3$_b$, 5.361 dd $J_{45}$ 1.0 H-4$_b$, 3.886 m H-5$_b$, 4.128 m $J_{56}$ 7.3 H-6$_b$, 4.093 m $J_{66'}$ −11.2 H-6'$_b$, 4.445 d $J_{12}$ 7.3 H-1$_a$, 4.033 ddd $J_{23}$ 9.4 H-2$_a$, 5.123 dd $J_{34}$ 8.0 H-3$_a$, 3.787 dd $J_{45}$ 8.3 H-4$_a$, 3.633 ddd $J_{56}$ 5.2 H-5$_a$, 4.501 dd $J_{66'}$ −11.9 H-6$_a$, 4.144 dd $J_{56'}$ 3.1 H-6'$_a$, 5.648 d $J_{2NH}$ 9.4 NH; propyl 3.387 and 3.783 2×ddd(1) $J_{HH}$'s 6.6, 9.4, −13.6 CH$_2$O, 1.575 m(2) CCH$_2$, 0.888 t(3) $J_{HH}$ 7.3 CH$_3$; acetates 2.154 s(3), 2.116 s(3), 2.077 s(3), 2.060 s(6), 1.974 s(3), 1.967 s(3), and $^{13}$C NMR (CDCl$_3$): acetates C=O 170.6, 170.4, 170.3, 170.1, 170.0 (2), 169.4, NCOCH$_3$ 23.3, OCOCH$_3$ 20.6, 20.5; 100.98 C-1$_b$, 100.98 C-1$_a$, 53.1 C-2$_a$, 75.7, 72.6, 72.2, 71.3, 70.8(2), 66.7 C-2$_b$ and C-3 to C-5$_{a+b}$, 62.5, 60.9 C-6$_{a+b}$, 69.2, 22.7, 10.4 propyl.

EXAMPLE 11

Removal of Polymer from DOX After Completion of Synthesis

4-Methylbenzyl 3,4,6-tetra-O-acetyl-2-O-(2,3,4,6-tetra-O-acetyl-α/β-D-mannopyranosyl)-α/β-D-mannopyranoside (VId)

PEG-DOX bound disaccharide VIa (1.19 g, 0.19 mmol) was hydrogenated on palladium black (450 mg) in acetic acid:water (1:1, 30 mL) at room temperature for 16 hrs. The catalyst was removed by filtration through a celite bed, rinsed subsequently well with aqueous (10%) methanol, and the filtrate and washings were evaporated at high vacuum <40°–45° C. The residue was co-evaporated with toluene (50 mL) and dried in vacuo. The residue was further recrystallized from ethanol (100 mL), and the solids were collected by filtration, rinsed with ethanol (25 mL) and t-butylmethyl ether (25 mL). The combined filtrate and washings were evaporated, the residue was dissolved in pyridine (5 mL), cooled in an ice bath under argon, acetic anhydride (2.5 mL) was added, and the mixture was stirred for 16 hrs. at room temperature. Then the liquids were removed by evaporation at high vacuum and the residue was chromatographed on a short silica gel column eluting with 2% methanol in dichloromethane to yield VId (α:β about 5:1). $^1$H NMR (CDCl$_3$): 4-methylbenzyl 7.2 m(4) aromatics, 4.685 d 4.512 d $J_{HH}$ −11.7 methylene, 2.349 s(3) CH$_3$, 4.895 d $J_{12}$ 1.7 H-1$_a$α, 4.974 d $J_{12}$ 1.8 H-1$_b$; acetates 2.147 s(3), 2.141 s(3), 2.070 s(3), 2.054 s(3), 2.033 s(3), 2.021 s(3), 2.001; Mass Spectrum MH$^+$ 741 and MNa$^+$ 763, Ac$_7$Hex$_2$$^+$ 619, Ac$_4$Hex$^+$ 331.

EXAMPLES 12 & 13

Capping of Unreacted Hydroxyls

EXAMPLE 12

PEG-DOXyl 3-O-allyl-4,6-O-benzylidene-2-deoxy-2-phthalimido-β-D-glucopyranoside (XVIIb)

A solution of PEGDOXyl 4,6-O-benzylidine-2-deoxy-2-phthalimido-β-D-glucopyranoside (XVIIa, 0.1 g) in a mixture cyclohexane:dichloromethane (1:1, 2 mL) and allyl trichloroacetimidate (0.2 g) was treated with BF$_3$.Et$_2$O in dichloromethane (0.08M, 0.5 mL) at 0° C. for 1 hours. Then diisopropylethylamine (0.1 mL) was added and t-butylmethyl ether (100 mL) precipitated XVIIb in 100% yield. $^1$H NMR (CDCl$_3$): aromatics 7.72–7.82, m, 4H, phthalimide; 7.0–7.5, m, 9H, aromatics; 5.918, m, 1H, $_{allyl}$; 5.585, s, 1H, benzylidene; 5.278, d, J8.62, 1H, H-1; 3.380, s, 3H, PEG CH$_3$.

EXAMPLE 13

Capping After Glycosylation of XVIIa with 2,3,4-Tri-O-benzyl-α-L-fucopyranosyl Bromide A mixture of XVIIa (2.0 g), tetraethylammonium bromide (1.16 g) and flame-dried molecular sieves (4A; 4 g) was stirred in anhydrous dimethylformamide (12 mL) for 2 hrs at room temperature under an atmosphere of argon. A solution of 2,3,4-tri-O-benzyl-α-L-fucopyranosyl bromide (2.4 g; 5 mmol) in dry dichloromethane (12 mL) was added dropwise and the reaction was sealed and stirred for a prolonged period of time, up to 400 hrs. The reaction mixture was transferred to a larger flask, precipitated with t-butylmethyl ether (600 mL), and the precipitate was filtered, and dried. Then it was dissolved in hot ethanol (100 mL), filtered again, and the filtered solution was cooled to give XVIIc (2.1 g; 98%). $^1$H NMR (CDCl$_3$): aromatics 7.0–7.82, m, 28H; 5.353, d, J 8.43 Hz, 1H, H-1 Glu; 5.58, s, 1H, benzylidene; 4.784, d, J3.33 Hz, 1H, H-1 Fuc; 3.380, s, 3H, PEG C$\underline{H}_3$; 0.855, d, J 6.66 Hz, C$\underline{H}_3$ Fuc.

This compound, XVIIc, was subjected to capping (allylation) as described in Example 12, to block any unfucosylated OH-3 of XVIIa so that this hydroxyl could not react in any subsequent reaction. As expected, the percentage of the unreacted hydroxy group was very small, and the presence of the allylic group was not detectable by NMR spectroscopy. Albeit the presence of this allylic cap can be detected by mass spectrometry after the PEG removal, it is not required for the continuation of the oligosaccharide synthesis. The synthesis continues by preparing another free hydroxyl for the next glycosylation.

While the present invention has been described with reference to specific embodiments thereof, it should be understood by those skilled in the art that various changes may be made and equivalents may be substituted without departing from the true spirit and scope of the invention. In addition, many modifications may be made to adapt a particular situation, material or composition of matter, process, process step or steps, or then present objective to the spirit of this invention without departing from its essential teachings.

REACTION SEQUENCES

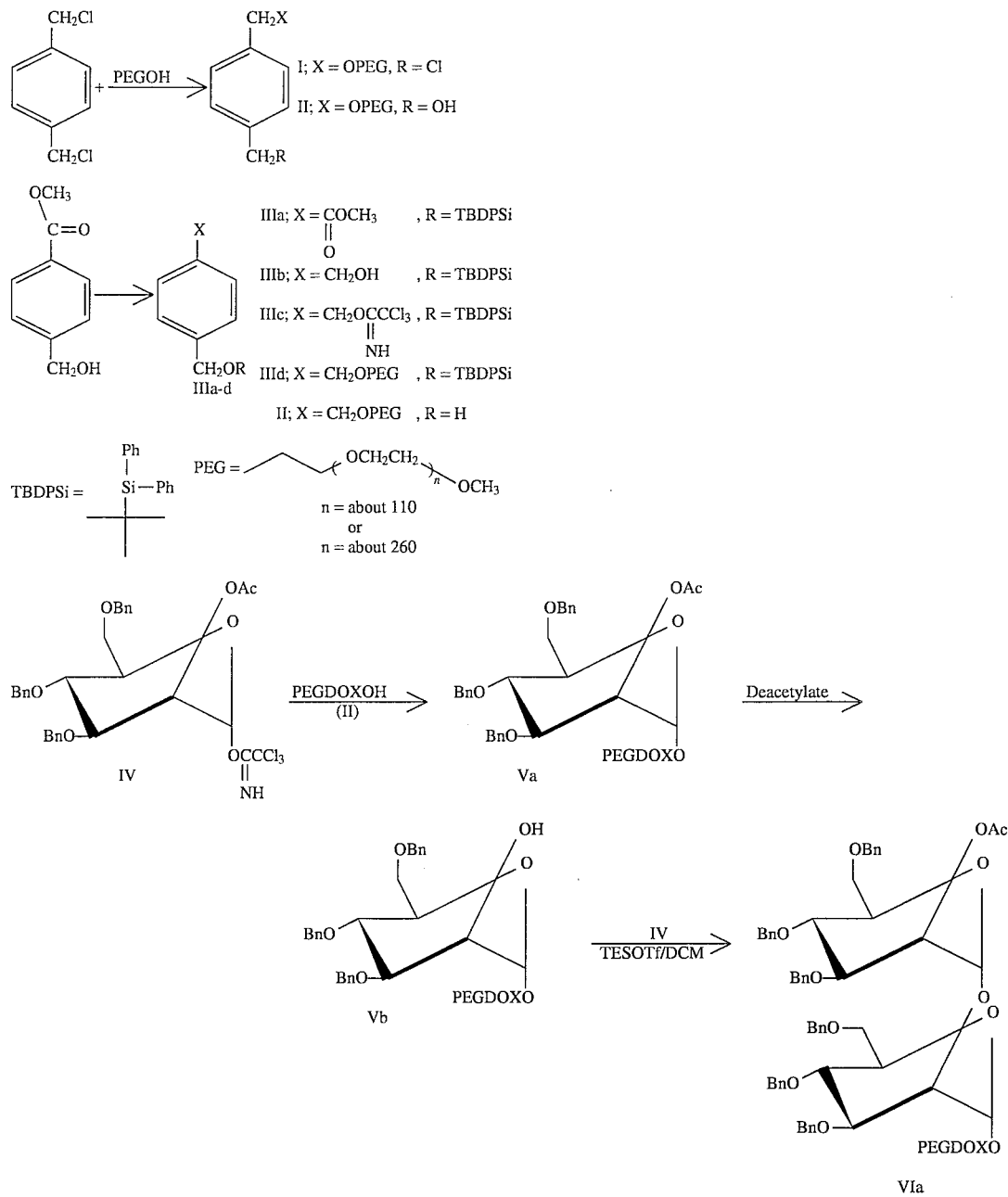

-continued
REACTION SEQUENCES
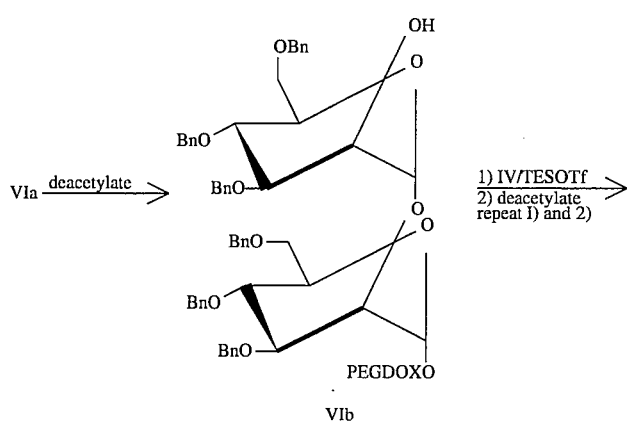
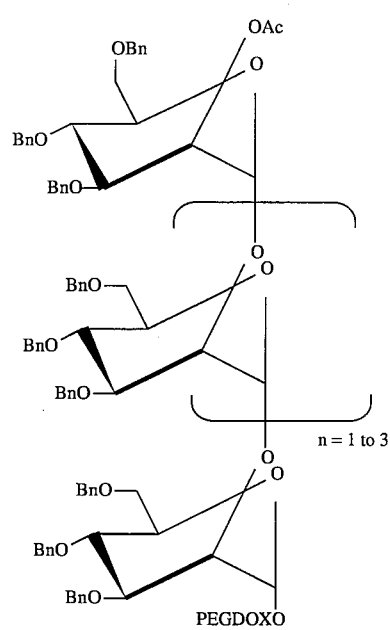
VIIa  n=1
VIIIa n=2
IXa   n=3
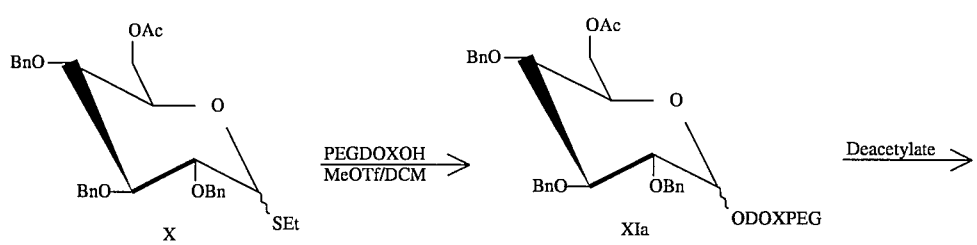

5,616,698
-continued
REACTION SEQUENCES
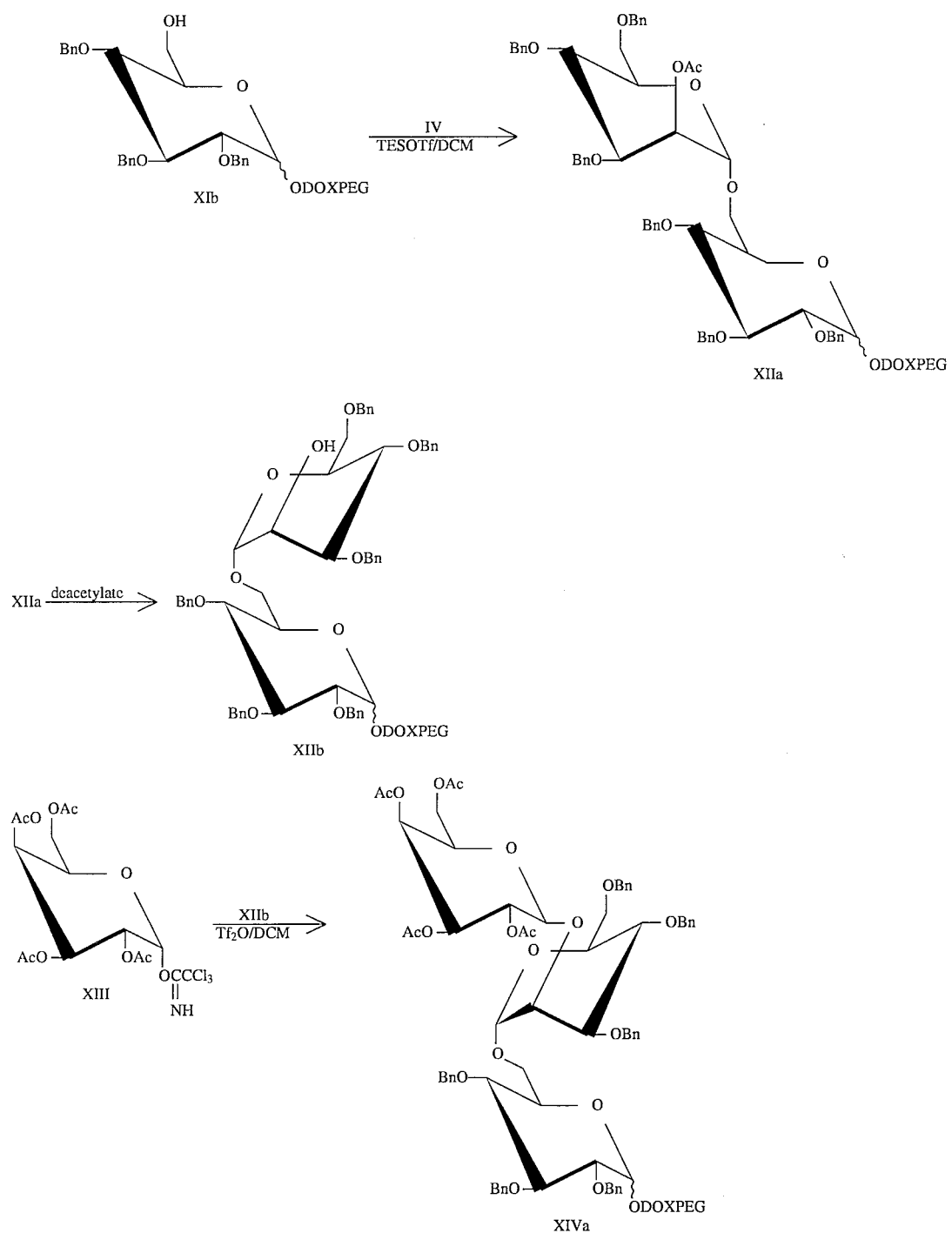

-continued
REACTION SEQUENCES

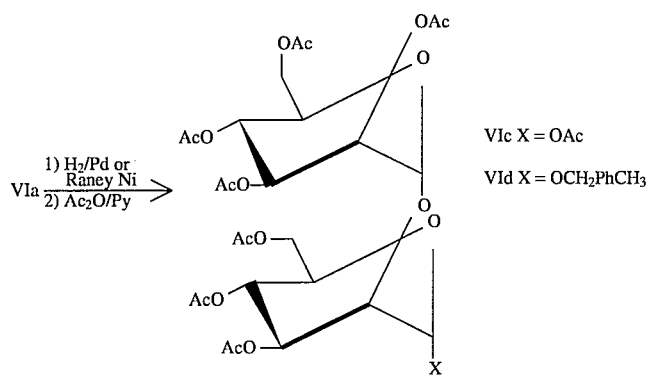

VIc X = OAc
VId X = OCH$_2$PhCH$_3$

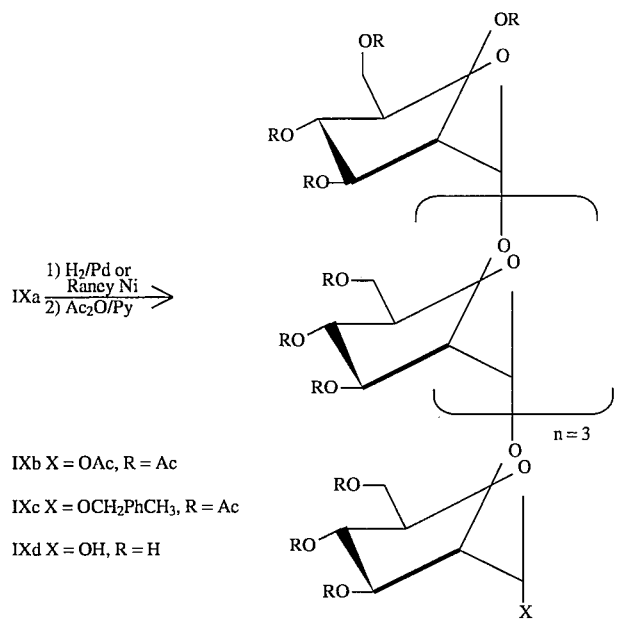

IXb X = OAc, R = Ac
IXc X = OCH$_2$PhCH$_3$, R = Ac
IXd X = OH, R = H

Attachment to Non-Anomeric Hydroxyl

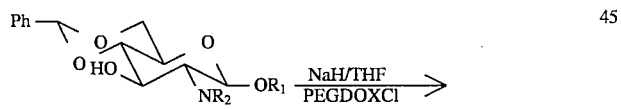

XVa R$_1$ = CH$_2$=CH—CH$_2$  R$_2$ = HAc
XVc R$_1$ = CH$_2$=CH—CH$_2$  R$_2$ = Phth

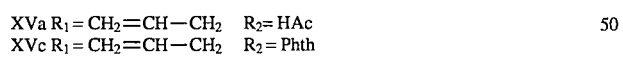

XVb R$_1$ = CH$_2$=CH—CH$_2$  R$_2$ = HAc
XVd R$_1$ = CH$_2$=CH—CH$_2$  R$_2$ = Phth

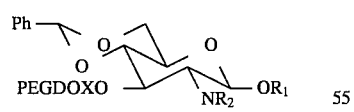

-continued
Attachment to Non-Anomeric Hydroxyl

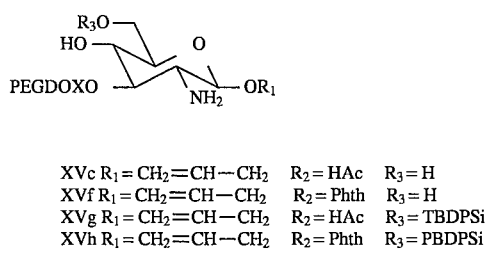

XVc R$_1$ = CH$_2$=CH—CH$_2$  R$_2$ = HAc   R$_3$ = H
XVf R$_1$ = CH$_2$=CH—CH$_2$  R$_2$ = Phth  R$_3$ = H
XVg R$_1$ = CH$_2$=CH—CH$_2$  R$_2$ = HAc   R$_3$ = TBDPSi
XVh R$_1$ = CH$_2$=CH—CH$_2$  R$_2$ = Phth  R$_3$ = PBDPSi XIII + $\xrightarrow{\text{XVh}}{\text{OTf}_2\text{O/DCM}}$

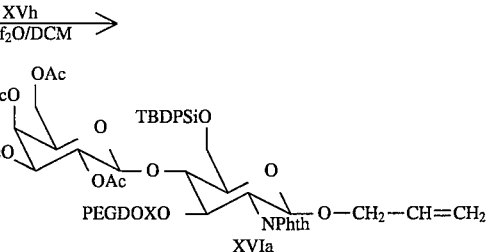

XVIa

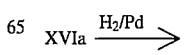

-continued
Attachment to Non-Anomeric Hydroxyl

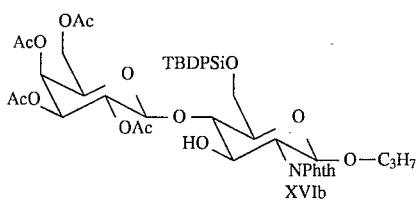

XVIb

Capping

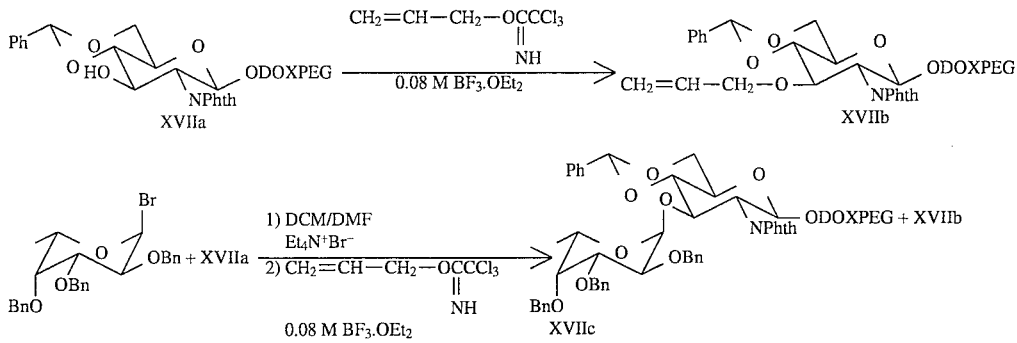

We claim:

1. A method for the preparation of oligosaccharides which comprises:
   a) reacting as a first reactant, a saccharide having at least one monosaccharide unit and having a carbohydrate hydroxyl group and as a second reactant a monomethylether of polyethylene glycol linked to a tether having one free hydroxyl group of a benzylic or allylic diol, and the linkage formed between the two reactants is an O-glycosidic linkage or an ether linkage;
   b) activating the saccharide-polyethylene glycol derivative reaction product for glycosylation;
   c) subjecting the activated saccharide-polyethylene glycol derivative reaction product to a glycosylation reaction through at least one addition of a glycosylating agent, while monitoring the reaction for completion;
   d) capping any non-glycosylated hydroxyl with a capping reagent which is more reactive than the glycosylating agent.

2. The method of claim 1 wherein said benzylic or allylic diol comprises α,α'-dihydroxy-p-xylene (HOCH$_2$C$_6$H$_4$CH$_2$OH).

3. The method of claim 1 wherein said capping agent is an alkylating agent.

4. The method of claim 3 wherein the alkylating agent comprises an alkenyl or aryl trichloroacetimidate.

5. The method of claim 1 wherein the reaction for completion is monitored by nuclear magnetic resonance spectrometry.

6. The method of claim 1 wherein the linkage is formed first by reacting α,α'-dichloroxylene with the monomethyl ether of polyethylene glycol, to form a second chloride having formula PEG—O—CH$_2$C$_6$H$_4$CH$_2$—Cl which is subjected to hydrolysis to provide PEG—O—CH$_2$C$_6$H$_4$CH$_2$—OH for connection to the saccharide through the hydroxyl.

7. The method as claimed in claim 1 wherein the hydroxyl of the saccharide is anomeric.

8. The method as claimed in claim 1 wherein the hydroxyl of the saccharide is non-anomeric.

9. The method as claimed in claim 1 wherein the monomethylether of polyethylene glycol is of average MW 5,000.

10. The method as claimed in claim 1 wherein the monomethylether of polyethylene glycol is average MW 12,000.

11. The method of claim 1 further comprising repeating steps b) through d) a plurality of times to form a polyethylene glycol-linker-oligosaccharide.

12. The method of claim 11 further comprising isolating the polyethylene glycol-linker-oligosaccharide as a solid.

13. The method of claim 12 wherein said isolating step comprises precipitation with an anhydrous ether.

14. The method of claim 12 wherein said isolating step comprises filtration under pressure of an inert gas.

15. The method of claim 14 wherein the filtration under pressure is performed in an apparatus excluding air humidity.

16. The method of claim 14 wherein the inert gas comprises anhydrous nitrogen or argon.

17. The method of claim 12 further comprising the steps of:
   purifying the solid; and
   releasing the oligosaccharide from the polyethylene glycol-linker so that the carbohydrate hydroxyl becomes free; and when desired
   releasing the oligosaccharide from the polyethylene glycol so that the linker becomes a p-methylbenzyl protecting group.

18. The method of claim 17 wherein said purification step comprises recrystallization.

19. The method of claim 17 wherein said releasing of said oligosaccharide from the polyethylene glycol in which the linker is transformed into p-methylbenzyl protecting group comprises hydrogenolysis over a catalyst.

20. The method of claim 19 wherein the catalyst comprises palladium metal.

21. The method of claim 17 wherein said releasing of said oligosaccharide from the polyethylene glycol is carried out by hydrogenolysis over a catalyst.

22. The method of claim 21 wherein the catalyst is either a precious metal or Raney nickel.

23. The reaction product obtained from:
   a) reacting as a first reactant, a saccharide having at least one monosaccharide unit and having a carbohydrate hydroxyl group and as a second reactant a monomethylether of polyethylene glycol linked to a tether having one free hydroxyl group of a benzylic or allylic diol, and the linkage formed between the two reactants is an O-glycosidic linkage or an ether linkage;

b) activating the saccharide-polyethylene glycol derivative reaction product for glycosylation;

c) subjecting the activated saccharide-polyethylene glycol derivative reaction product to a glycosylation reaction through at least one addition of a glycosylating agent, while monitoring the reaction for completion; and d) capping any non-glycosylated hydroxyl with a capping reagent which is more reactive than the glycosylating agent.

24. The product as claimed in claim 23 wherein said benzylic or allylic diol comprises α,α'-dihydroxy-p-xylene (HOCH$_2$C$_6$H$_4$CH$_2$OH).

25. The product of claim 23 wherein the linkage is formed first by reacting α,α'-dichloroxylene with the monomethyl ether of polyethylene glycol, and the second chloride having formula PEG—O—CH$_2$C$_6$H$_4$CH$_2$—Cl is subjected to hydrolysis to provide PEG—O—CH$_2$C$_6$H$_4$CH$_2$—OH for connection to the saccharide through the hydroxyl.

26. The product of claim 23 wherein the hydroxyl of the saccharide is anomeric.

27. The product of claim 23 wherein the hydroxyl of the saccharide is non-anomeric.

28. The product of claim 23 wherein the monomethylether of polyethylene glycol is of average MW 5,000.

29. The product of claim 23 wherein the monomethylether of polyethylene glycol is of average MW 12,000.

30. The product of the process of claim 23 wherein the process further comprises repeating steps b) through d) a plurality of times to form a polyethylene glycol-linker-oligosaccharide.

31. The product of the process of claim 30 wherein the process further comprises isolating the polyethylene glycol-linker-oligosaccharide as a solid.

32. The product of the process of claim 31 wherein the process further comprises purifying the solid.

33. A composition of formula:

OS—DOX—PEG wherein

OS is an oligosaccharide;

DOX is an α,α'-dioxyxylyl ether of formula —O—CH$_2$(C$_6$H$_4$)CH$_2$O—; and

PEG is a polyethyleneglycol monomethyl ether having an average molecular weight of from about 5,000 to about 12,000.

34. The composition of claim 33 wherein the polyethyleneglycol monomethyl ether has an average molecular weight of about 5,000.

35. The composition of claim 33 wherein the polyethyleneglycol monomethyl ether has an average molecular weight of about 12,000.

* * * * *